United States Patent [19]

Cole et al.

[11] Patent Number: 5,197,945

[45] Date of Patent: Mar. 30, 1993

[54] ALGINATE WOUND DRESSING OF GOOD INTEGRITY

[75] Inventors: Susan M. Cole, Minneapolis; David L. Nelson, Woodbury, both of Minn.

[73] Assignee: Minnesota Mining and Manufacturing Company, St. Paul, Minn.

[21] Appl. No.: 820,343

[22] Filed: Jan. 14, 1992

Related U.S. Application Data

[63] Continuation of Ser. No. 622,433, Dec. 5, 1990, which is a continuation-in-part of Ser. No. 484,068, Feb. 23, 1990, abandoned, which is a continuation of Ser. No. 200,711, May 31, 1988, abandoned.

[51] Int. Cl.$^5$ .................. A61F 13/00; A61F 15/00
[52] U.S. Cl. ........................ 602/49; 602/42; 602/45; 604/367; 28/105
[58] Field of Search ............ 28/104, 105; 602/42, 602/45, 49; 604/304, 367

[56] References Cited

U.S. PATENT DOCUMENTS

| | | | |
|---|---|---|---|
| 3,449,809 | 6/1969 | Shin | 28/72.2 |
| 3,485,706 | 12/1969 | Evans | 261/72 |
| 3,493,462 | 2/1970 | Bunting, Jr. et al. | 161/169 |
| 3,494,821 | 2/1970 | Evans | 161/169 |
| 3,546,755 | 12/1970 | Lynch, Jr. | 28/72.2 |
| 3,911,116 | 10/1975 | Balassa | 424/180 |
| 4,104,115 | 8/1978 | Prouse et al. | 162/100 |
| 4,421,583 | 12/1983 | Aldred et al. | 156/167 |
| 4,499,139 | 2/1985 | Schortmann | 428/245 |
| 4,562,110 | 12/1985 | Tong | 428/284 |
| 4,630,603 | 12/1986 | Greenway | 128/156 |
| 4,665,597 | 5/1987 | Suzuki et al. | 428/134 |
| 4,695,500 | 9/1987 | Dyer et al. | 428/134 |
| 4,704,113 | 11/1987 | Schoots | 604/379 |
| 4,755,421 | 7/1988 | Manning et al. | 428/224 |
| 4,808,467 | 2/1989 | Suskind et al. | 28/104 |
| 4,902,564 | 2/1990 | Israel et al. | 28/104 |

FOREIGN PATENT DOCUMENTS

WO80/02300 10/1980 PCT Int'l Appl. .
653341 5/1951 United Kingdom .
1283399 7/1972 United Kingdom .
1394741 5/1975 United Kingdom .

OTHER PUBLICATIONS

R. W. Moncrieff, "Man-made Fibres" (1975) pp. 300-306.

Kirk-Othmer, *Encyclopedia of Chemical Technology*, vol. 16, John Wiley & Sons, pp. 768-773 (1981).

Francis C. Zevnik, "Waterjet Entanglement in Perspective", presented at the IMPACT 88 seminar, Florida (Mar. 10, 1988).

"Fiber Bonding", *Pulp and Paper Chemistry and Chemical Technology*, 3rd Ed. vol. II, John Wiley & Sons, pp. 915-963.

*Primary Examiner*—Paul Prebilic
*Attorney, Agent, or Firm*—Gary L. Griswold; Walter N. Kirn; Dale A. Bjorkman

[57] ABSTRACT

A wound dressing of alginate staple fibers has improved integrity when its fibers have been hydroentangled. Even when its basis weight is as low as 50 g/m$^2$, the resulting wound dressing, when saturated with saline fluids, can be removed by forceps from a wound as a single piece, having little or no residue in the wound. At basis weights below 50 g/m$^2$, the wound dressing preferably includes reinforcing fibers such as rayon.

21 Claims, 5 Drawing Sheets

ALGINATE WOUND DRESSING OF GOOD INTEGRITY

This application is a continuation of U.S. Ser. No. 07/622,433 filed Dec. 5, 1990 which is a continuation-in-part of U.S. Ser. No. 07/484,068 filed Feb. 23, 1990 now abandoned which is a continuation of U.S. Ser. No. 07/200,711 filed May 31, 1988 now abandoned.

BACKGROUND OF THE INVENTION

1. Field of the Invention

The invention relates to wound dressings of alginate fiber and to the use of the dressings both for keeping a wound bed moist and for packing a deep wound.

2. Description of the Related Art

U.K. Pat. Speck. No. 653,341 (Bonniksen) which was published May 16, 1951 says: "The use of calcium alginate materials, made up into wool, gauze, foam, and the like, in surgery is now well known. They are used, because of their absorbability in the body, to control hemorrhage, fill 'dead space' after the removal of organs or massive tissue, act as tissue isolating films, and externally as burn, ulcer and wound covers. They fill a recognized and important need, their properties having been described in detail by George Blaine in the Annals of Surgery for Jan., 1947" (page 2, lines 5-23). The Bonniksen specification further says that when a calcium alginate dressing is placed on an external wound, it swells in and is very slowly dissolved by the body fluids.

U.K. Pat. Spec. No. 1,394,741 (Franklin et al.) which was published May 21, 1975 says that calcium alginate materials have long been used as hemostatic surgical dressings, usually after being knitted into gauze and then replacing part of the calcium content by a more soluble cation such as sodium. Soluble cations are said to enable the alginate to disperse more readily in body fluids and tissues. A knitted alginate is currently being marketed as Ultraplast TM styptic gauze wound dressing by Wallace, Cameron & Co. Ltd., Glascow, Scotland.

U.S. Pat. No. 4,562,110 (Tong) says that the knitting of the dressing of the Franklin specification "has usually involved handling problems and has been carried out batchwise which is rather inefficient and uneconomic resulting in a costly and wasteful production process" (col. 1, lines 38-48). In the invention of the Tong patent, calcium alginate fiber material is first converted into the sodium/calcium mixed salt form, dried, and then "made up into a tow suitable for swab production or alginate wool or into the form of a non-woven wadding suitable for use as a medical or surgical dressing" (col. 1, lines 49-58).

The Tong patent discusses a process for making an alginate dressing as disclosed in International Pat. Appl. No. PCT/GB30/00066 (Courtaulds Ltd.) in which a tow of "calcium alginate fibres or filaments is passed in a flow of water through a spreading device, such as a device with a 'fish tail' outlet, and the spread band or sheet produced is fed forwards and deposited on a liquid permeable conveyor, such as Fourdrinier wire mesh conveyor, moving at a slower speed so that the fibres are overlaid in a substantially uniform layer or sheet forming a web which is then dried to provide a unitary non-woven alginate fabric. As a result of the overlaying, the fibres become crimped or looped and cross over each other in the web so that a parallel orientation thereof is destroyed" (col. 2, lines 40-59). This produces "a dried web of intersecting fibres or filaments bonded together at their cross-over points to provide a strong unitary structure" (col. 3, lines 18-23).

The Tong patent says that the process of the Courtaulds PCT application produces "a relatively harsh fabric likely to be very stiff and to have poor handling qualities, especially if one attempts to make up such webs into thick or multilayer fabrics" (col. 5, lines 7-15). The invention of the Tong patent concerns a process similar to that of the Courtaulds PCT application except including "at least one controlled treatment step which is effective to eliminate or reduce bonding of the overlaid fibres at their points of contact or intersection" (col. 4, lines 26-33).

U.S. Pat. No. 4,421,583 (Aldred et al.) corresponds to the Courtaulds PCT application.

Although it is not known whether alginate fabrics are being manufactured in accordance with any of the above-discussed processes, a carded web of alginate fibers is being marketed as Steriseal Sorbsan TM surgical dressing by N. I. Medical, Redditch, Worcestershire, England, and a carded and needle-tacked web of alginate fibers is being marketed as Kaltostat TM haemostatic wound dressing by Cair Ltd., Aldershot, Hatt, England. Alginate tow is also marketed by each of those companies under the same tradenames for use as wound dressings, and especially for surgical packing.

Except for the knitted Ultraplast TM and the needle-tacked Kaltostat TM wound dressings, each of the aforementioned commercial alginate products has poor integrity and hence is difficult to handle. However, the needle-tacked Kaltostat TM wound dressing has a relatively high basis weight, about 160 g/m$^2$, and is not as supple as would be desired for most applications. It is assumed that the needle-tacked Kaltostat TM dressing is not offered at lower basis weights, because it then would be rather weak. Additionally, because alginate fibers are highly absorbent, dressings based on high basis weight webs of the fibers would be more likely to desiccate a wound if applied to the wound in a dry condition. The manufacturer of the needle-tacked Kaltostat TM dressing avoids this problem by recommending that the dressing be moistened before application to the wound.

Except for the knitted Ultraplast TM wound dressing, the commercial alginate wound dressings mentioned above are weak and tend to shed fibers. Because of their weakness, skill is required to apply the dressing to wounds, and handling problems are aggravated when ones fingers are not completely dry.

Although the knitted Ultraplast TM wound dressing has good integrity when dry, it becomes weak and loses its integrity when saturated with saline or body fluids. This loss of integrity causes the Ultraplast TM wound dressing to disintegrate while being lifted from a wound (as do other commercial alginate dressings cited above), necessitating that it be picked out in tiny pieces or removed from the wound by irrigation. Because removal by irrigation is a complicated and messy process that requires a substantial degree of skill, users prefer wound dressings that can be lifted from a wound in a single piece.

While we are not aware of any rigorous clinical testing to show any medicinal effect from dressing or packing a wound with an alginate fabric, clinical testing has established that the healing of a wound is enhanced by keeping the wound moist, and alginate dressings and packings admirably retain moisture. Alginate fibers also release well from human tissue.

OTHER PRIOR ART

U.S. Pat. No. 4,704,113 (Schoots) says that two important functions of a surgical or wound dressing are the ability to absorb and hold liquid and the ability to wick and transfer exudate of a wound away from the wound site, but that known dressings which have good absorbtive capability have relatively poor fluid transfer characteristics. The Schoots patent concerns dressings made in accordance with the teachings of U.S. Pat. No. 3,485,706 (Evans) to provide hydroentangled fabrics that "comprise fibers locked into place by fiber interaction to provide a strong cohesive structure which maintains its structural integrity without the need for adhesive binders or filament fusing . . . accomplished by first preparing a loose layer of fibers and then passing the layer through an entangler where it is treated with liquid, jetted at a pressure of at least 200 psig. from one or more rows of small orifices" (col. 2, lines 7-29).

Each of the Schoots and Evans patents identifies a large number of fibers that are said to be useful, but neither mentions alginate fibers. Example 1 of Schoots identifies eight fabrics, each made of two different fibers such as a mixture of rayon and polyester fibers.

SUMMARY OF THE INVENTION

The invention provides an alginate wound dressing having sufficient integrity to be lifted in one piece from a wound even though it has become saturated with blood or other saline fluids. This can be accomplished at surprisingly low basis weight, e.g., as low as about 50 g/m$^2$. Because of the improved integrity, alginate wound dressings of the present invention can be produced in a variety of basis weights, permitting one to select a dressing of the desired absorbency, thus minimizing the danger of desiccating the wound. Furthermore, when a novel alginate wound dressing of low basis weight is suitable for a particular wound, the dressing can be cost effective in spite of the rather high current cost of alginate fibers.

Briefly, the invention concerns a wound dressing comprising a nonwoven fabric of alginate staple fibers, which fabric is substantially free from any adhesive binder or of interfusing of fibers at their crossing points. Thus, the web is held together only by friction and any naturally occurring hydrogen bonding. The fabric of the invention differs from prior alginate wound dressings in that its fibers are sufficiently entangled that a plot of its tensile strength when dry vs. its basis weight lies above line 12 of FIG. 1 of the drawing when the fabric is dry and lies above line 22 of FIG. 2 when the fabric is saturated with saline water. Furthermore, the fabric has sufficient integrity to permit it to be slit by a continuous process to desired widths, a procedure generally not feasible in the production of the above-mentioned commercial alginate webs because of their poor integrity.

The fabric of the present invention comprises at least 35% by weight of alginate fibers. Most preferably, the fabric comprises at least 50% by weight alginate fibers. The balance of the fabric may be any fiber suitable for use in wound dressings, but is most preferably a fiber that will provide a reinforcing component to the fabric.

This invention also relates to fabrics made in a layered fashion, wherein a web of fibers not predominantly composed of alginate fibers is provided as a single layer and is overlaid by a predominantly alginate fiber web, followed by hydroentanglement. Wound dressing fabrics made using this configuration may contain a comparatively small amount of alginate fiber by weight while still manifesting many of the desired properties of alginate dressings, because the alginate fiber is more efficiently available for direct interface with the wound site. Such layered dressings may have an alginate content of as low an amount as will provide the desirable slippery properties of alginate dressings. Preferably, such fabrics will contain about 10% by weight of alginate fibers. Alternatively, the layer that is not predominantly alginate fiber may be "sandwiched" between predominantly alginate fiber layers, so that either side of the fabric is appropriate for contacting the wound site.

Direct contact of the wound site by alginate fibers is particularly desirable because the alginate is highly fluid absorbent and is very slippery when wet. Because the dressing is slippery, it experiences less adhesion to the wound site and may be removed for changing or wound inspection more easily than standard cotton gauze dressings. Dressings made using alginate fibers are preferably saturated with wound exudate or soaked with saline and will keep the wound moist, which enhances the healing process. Alginate based dressings also absorb more saline than cotton dressings, and therefore take longer to dry out.

The novel alginate wound dressing can be made by the steps of
(a) processing staple alginate fibers to provide a nonwoven web and
(b) hydraulically entangling, preferably hydroentangling, the alginate fiber webs into a fabric that has good integrity.

While being hydraulically entangled, the nonwoven web is preferably supported by an apertured member, such as a perforated plate or a screen. By using screens of various sizes, the hydraulically entangled alginate wound dressings of the invention can have various degrees of openness. When a novel alginate dressing has a highly open structure and is saturated with saline fluids, it has a translucent quality in contact with a wound which permits the wound to be inspected without removing the dressing. Like prior alginate dressings, those of the invention do not swell appreciably in pure water but become highly swelled in saline fluids.

Because of the gelatinous nature of their fibers when saturated with saline fluids, the novel alginate wound dressings, when impregnated with therapeutic agents, provide controlled release of those agents into the wound. Useful therapeutic agents include antimicrobials, growth factors, and nutrients.

DETAILED DISCLOSURE

Because alginate fibers are highly absorbent, it may be desirable in some cases to saturate the novel wound dressing with saline water before applying it to a wound, thus minimizing any danger of desiccating the wound. When its basis weight is low, the novel alginate wound dressing preferably includes a small percentage of reinforcing fiber such as rayon to permit it to be handled easily while saturated with saline water.

The novel alginate wound dressings are drapable and easy to use at basis weights up to about 200 g/m$^2$, and can be drapable at higher basis weights when they have good openness. However, at basis weights substantially above 150 g/m$^2$, the novel dressings may be unduly expensive at the current cost of alginate fibers. Furthermore, alginate wound dressings having higher basis weights would be more likely to desiccate the wound. On the other hand, at basis weights much below 20 g/m$^2$, the novel alginate wound dressings may be too weak to be manufactured at commercially viable production rates unless they include reinforcing fibers and probably would need to be die-cut to desired widths instead of being slit. Preferably, the fabrics of the present invention have a basis weight of between about 50 and 200 g/m$^2$. Most preferably, the fabrics have a basis weight of between about 80 and 180 g/m$^2$.

At basis weights of 60 g/m$^2$ or more, the novel alginate fabric of the invention, even without reinforcing fibers, has sufficient integrity to permit it to be converted into strips as narrow as about 5 mm using a continuous slitting process. Narrow width dressings are desirable as wound packing materials. In contrast, none of the above-mentioned commercial alginate webs is available in widths less than about 5 cm.

Preferably the alginate staple fibers of the novel wound dressings are from 2 to 10 cm in length. Longer fiber lengths are difficult to convert into uniform nonwoven webs that can be hydraulically entangled to produce the dressings of the present invention. Staple fibers shorter than 2 cm in length are difficult to convert into nonwoven webs of sufficient integrity to permit them to be hydraulically entangled.

Further improvement to the integrity of entangled alginate wound dressings of the invention can be achieved by incorporating fibers of greater strength such as rayon, cotton, or nylon staple fibers or other fibers such as chitosan staple fibers. Incorporation can be accomplished by blending the fibers during web formation or by overlaying the nonwoven alginate web with a nonwoven web of the reinforcing fiber prior to hydroentanglement.

It may be desirable to micro-crepe the entangled alginate wound dressings of the invention to enhance their absorptive capability. A suitable technique is taught in the above-cited U.S. Pat. No. 4,704,113.

The wound dressing fabric of the present invention can incorporate a significant amount of alternative fibers to afford greater strength and reduce cost of the overall dressing. Specifically, alternative fibers may constitute up to 65% by weight of the fabric, with the fabric still affording the desired properties of slipperiness and moisture retention that are so advantageous in alginate fiber dressings. Alginate webs are by nature weak, particularly when immersed in saline, because they swell in the presence of certain cations. Blending the alginate fibers with fibers that do not swell in saline will increase the strength of the overall fabric, while retaining the benefits of the alginate fiber.

Dressings containing alginate fibers have excellent moisture retention properties, which is clinically significant because wound dressings that retain fluids do not need to be changed as often as dressings that dry out quickly. The retention of fluids by alginate dressings is superior to other dressings because these dressings start out with a larger amount of fluid and thus have more to evaporate. Dressings having at least 35% alginate content have a significantly longer fluid retention period, and thus are particularly useful as wound dressings.

The level of energy used in the hydroentanglement process also plays an important role in determining the wet and dry strength of the webs. Under moderate hydroentanglement conditions, the web obtains no advantage over needle-tacked webs because the fibers are not entangled enough to provide superior strength. When higher energy is expended in the entanglement process, a great increase in strength of the fabric is observed. Preferably, hydroentanglement is accomplished by at least one pass having a water pressure of at least 6200 kPa, more preferably more than 9600 kPa and most preferably more than 10300 kPa. Conveyor speed of the hydroentangler is also a factor in delivering energy to a unit area of web. While even at fast conveyor speeds, the above amounts of water pressure will achieve satisfactory entanglement, a conveyor speed of no more than about 50 meters per minute, and more preferably no more than about 20 meters per minute, is desirable. It is understood as a general principle that slower conveyor speeds allow a somewhat lower amount of water pressure to be used in the hydroentanglement process because each unit area of web will be subjected to the same amount of energy.

Fabrics of the present invention may be sterilized by methods such as ethylene oxide sterilization, ionizing radiation and the like. Although some forms of sterilization, particularly radiation treatment, will adversely affect the observed tensile strength of the ultimate fabric, even sterilized product exhibits superior strength characteristics to alginate dressings previously available.

The alginate wound dressings of the invention may be used to pack deep wounds or as absorbent contact layers on shallow wounds. In either case, the alginate dressing should be secured or covered with a material, e.g. a film dressing such as a conventional polyurethane transparent film dressing, a hydrocolloid dressing, a gauze dressing, or a bandage wrap such as gauze or a compression wrap.

DETAILED DESCRIPTION OF THE DRAWING

Figure 1:
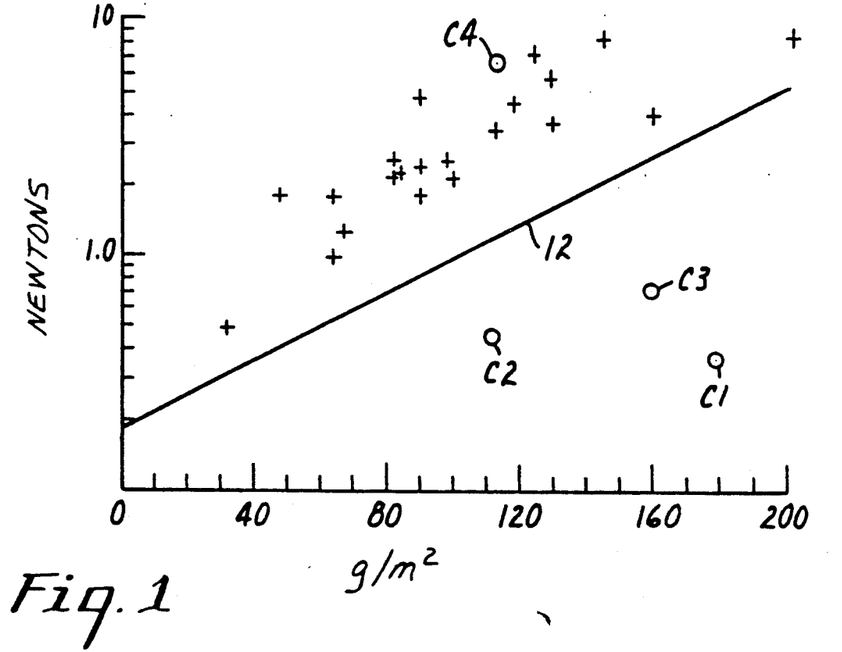
FIG. 1 plots tensile strength vs. basis weight for representative alginate wound dressings of the invention when dry in comparison to alginate wound dressings of the prior art.

Referring to FIG. 1, points 10 indicated by "+" represent data of Table I below showing the relationship between tensile strength and basis weight for hydroentangled alginate wound dressings of Examples 1-21 that were tested when dry ("Web Dry Strength" as described below). Points C1, C2, C3 and C4 represent data indicated by "o" to show the same relationship for certain alginate fabrics which are representative of the prior art (Comparative Examples C1, C2, C3 and C4, respectively, identified below). When the fibers of an alginate fabric are sufficiently entangled to achieve the objectives of the invention, a plot of its tensile strength when dry vs. basis weight lies above line 12 of FIG. 1.

Figure 2:
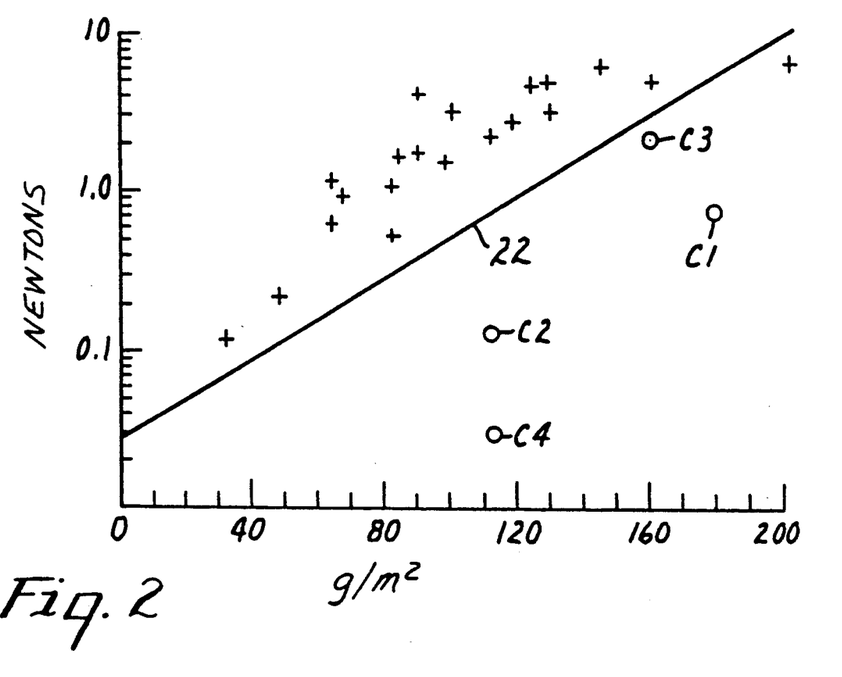
FIG. 2 plots tensile strength vs. basis weight for the same wound dressings when saturated with saline water.

In FIG. 2, points 20 indicated by "+" show data of Table I on tensile strength vs. basis weight obtained by testing the same hydroentangled alginate fabrics of Examples 1-21 when saturated with saline water ("Web Wet Strength" as described below). Points C1, C2, C3 and C4 indicated by "o" were obtained by testing Comparative Examples C1-C4. When the fibers of an alginate fabric are sufficiently entangled to achieve the objectives of the invention, a plot of its tensile strength when saturated with saline water vs. basis weight lies above line 22 of FIG. 2.

FIGS. 3-9 show data tabulated in Tables V and VI.

Figure 3:
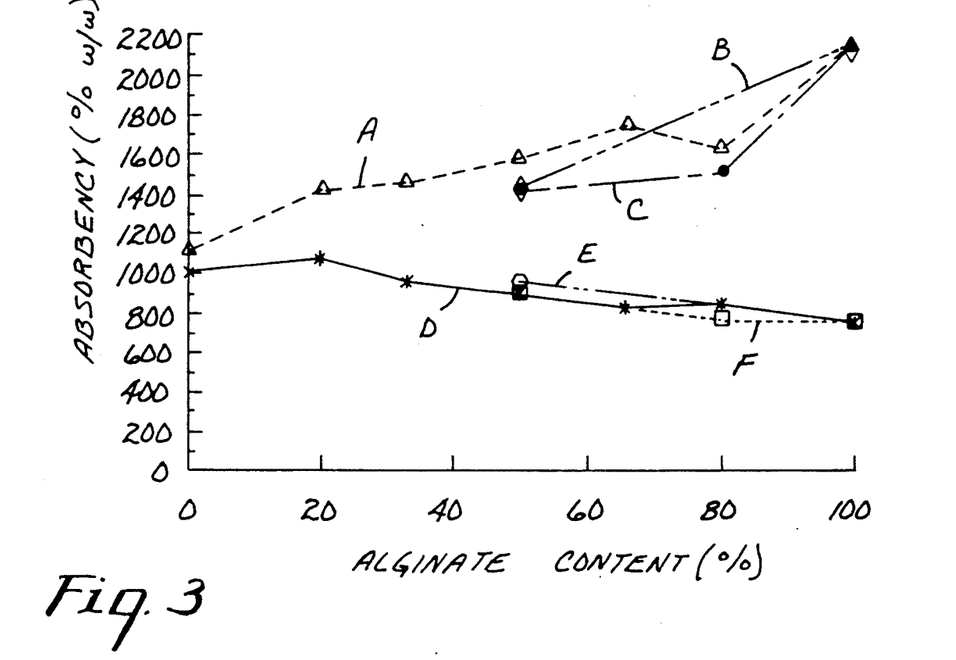
FIG. 3 plots alginate content vs. absorbency of water and saline.

FIG. 3 shows the relationship between alginate content of fabrics vs. absorbency of water and saline. Saline is representative of cation containing fluids, such as body fluids and wound exudate, for evaluating fluid uptake of these fabrics. Line A shows absorbency of saline for rayon/alginate blends, line B shows absorbency of saline for nylon/alginate blends and line C shows absorbency of saline for cotton/alginate blends. Similarly, line D shows absorbency of water for rayon/alginate blends, line E shows absorbency of water for nylon/alginate blends and line F shows absorbency of water for cotton/alginate blends. As alginate content of the fabric increases, the uptake of saline also increases. This relationship holds true for blends of nylon, rayon and cotton. This enhancement of absorbency is not observed for water, but only in cation-containing fluids. This enhancement is not significant for low alginate content blends.

Figure 4:
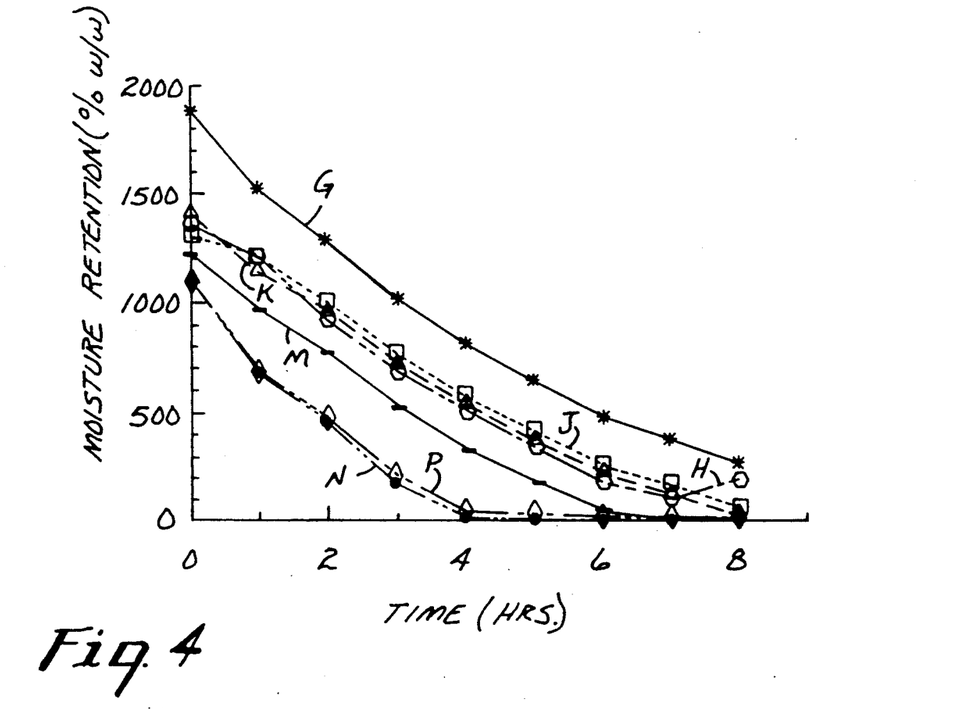
FIG. 4 plots moisture retention of various blends of rayon:alginate vs. time.

The significant effect of this enhanced saline uptake is shown in FIG. 4, which graphically illustrates the clinical value of incorporating alginates in fiber blends. The graph plots time vs. moisture retention of various rayon/alginate blends. Line G is a 100% alginate fabric, line H is a 20:80 rayon/alginate blend, line J is a 33:67 rayon/alginate blend, line K is a 50:50 rayon/alginate blend, line M is a 67:33 rayon/alginate blend, line N is a 80:20 rayon/alginate blend and line P is a 100% rayon fabric. Materials having more than 35% alginate fiber would be expected to retain moisture for greater than 6 hours, an important aid in providing a healing environment for the wound.

Figure 5:
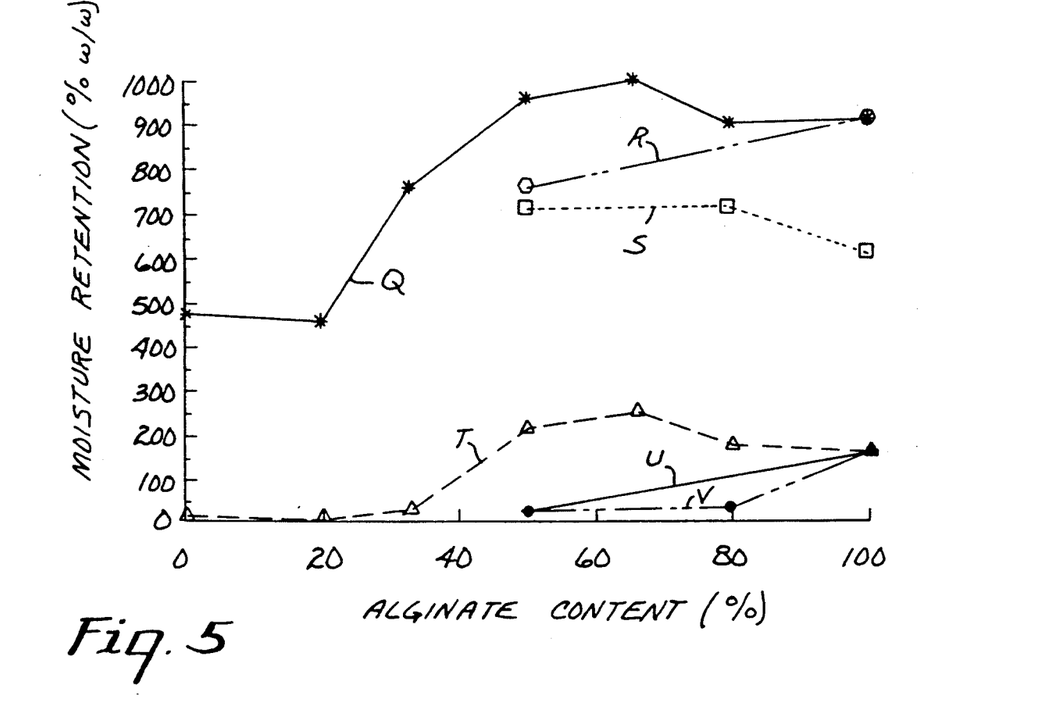
FIG. 5 plots amount of moisture retention vs. alginate content at 2 hours and 6 hours.

FIG. 5 better shows the differentiation that the amount of alginate content can make in overall moisture retention. This graph plots alginate content of fabrics vs. moisture retention for fabric blends at two time measurement points. Line Q shows the moisture retention of rayon/alginate blends at two hours, line R shows nylon/alginate blends at two hours, line S shows cotton/alginate blends at two hours, line T shows rayon/alginate blends at six hours, line U shows nylon/alginate blends at six hours and line V shows cotton/alginate blends at six hours. Fiber blends having more that about 35% alginate content show better moisture retention.

Figure 6:
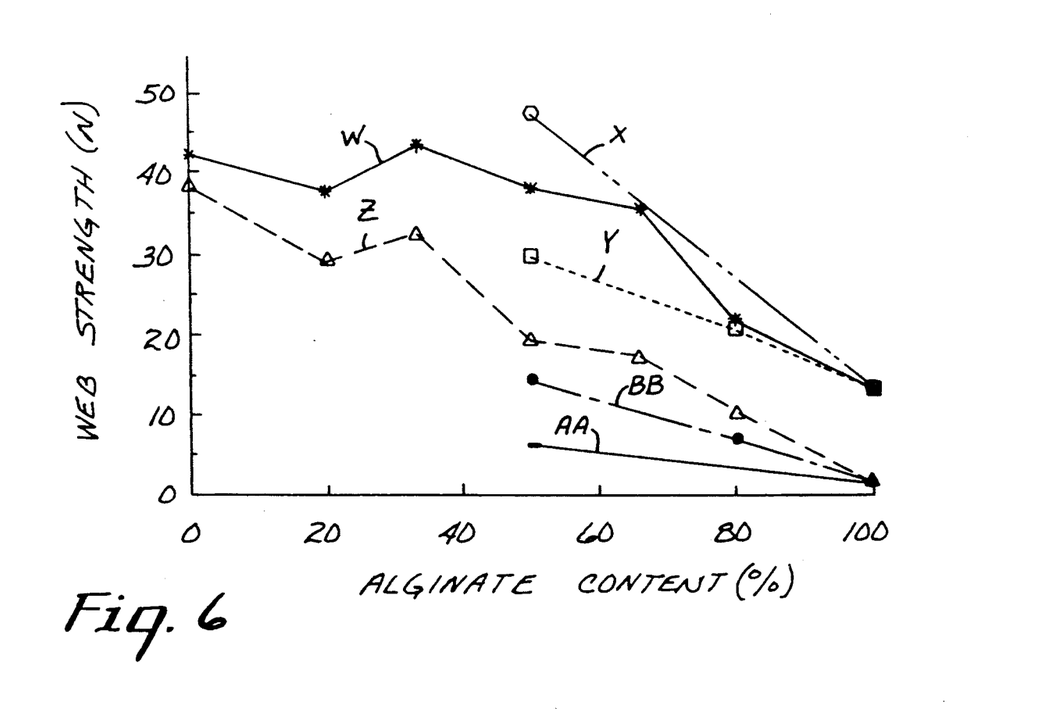
FIG. 6 plots alginate content vs. web strength for a number of fiber selections.

FIG. 6 shows that as the amount of non-alginate fiber increases in the fabric, the wet strength of the fabric in saline also increases. Line W shows web strength of water saturated rayon/alginate blends, line X shows web strength of water saturated nylon/alginate blends, line Y shows web strength of water saturated cotton/alginate blends, line Z shows web strength of saline saturated rayon/alginate blends, line AA shows web strength of saline saturated nylon/alginate blends and line BB shows web strength of saline saturated cotton/alginate blends. This strengthening effect appears to level off as alginate content drops below about 35%.

Figure 7:
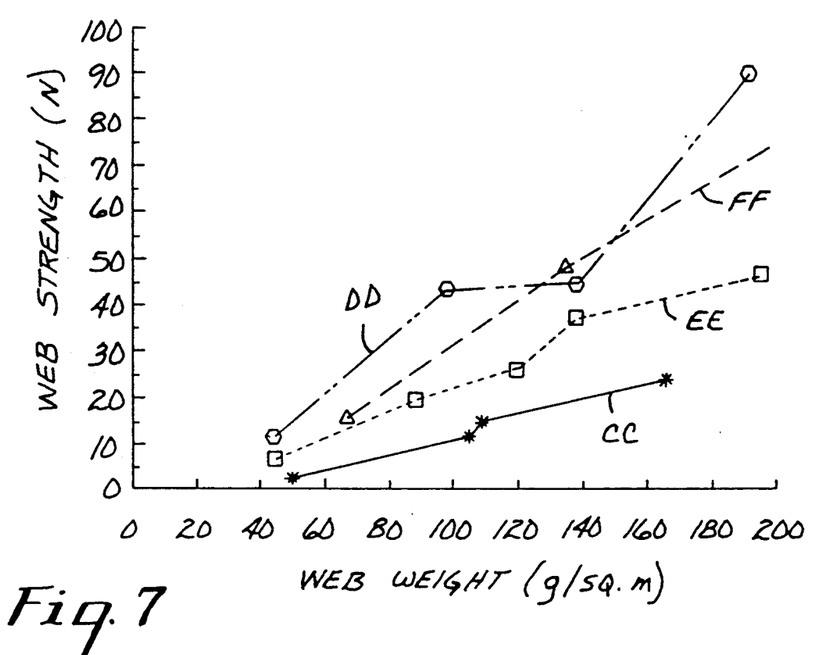
FIG. 7 plots web weight vs. dry web strength for 100% alginate and 50:50 blends of alginate with rayon, cotton and nylon.
Figure 8:
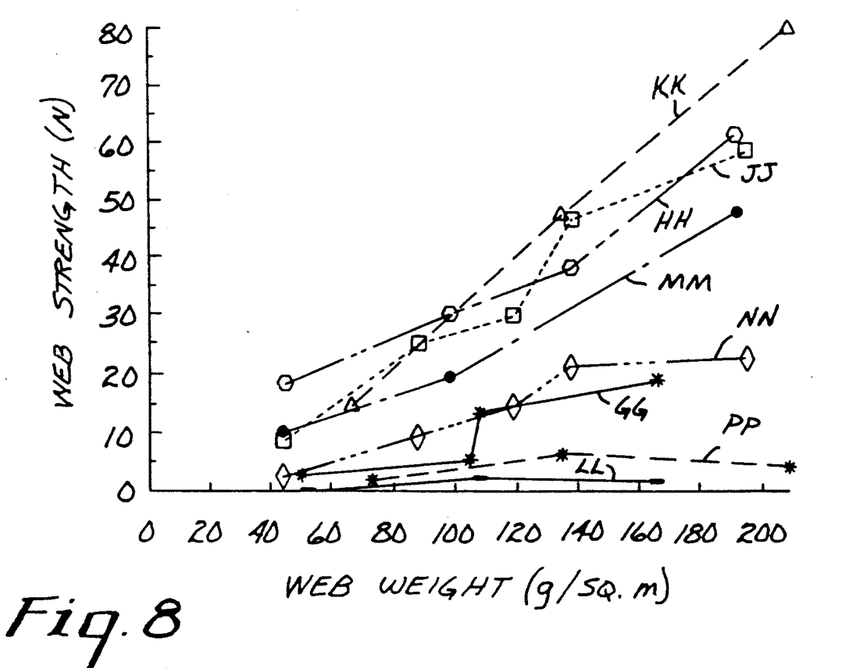
FIG. 8 plots web weight vs. wet web strength in water and saline for 100% alginate and 50:50 blends of alginate with rayon, cotton and nylon.

FIG. 7 and FIG. 8 show that the increase in strength of the fabric as other fibers are incorporated in increasing amounts holds true for both dry strength and wet strength measurements across a range of web weights, whether the additional fiber is cotton, rayon or nylon. In FIG. 7, line CC shows web strength of 100% alginate fabrics, line DD shows web strength of 50:50 rayon/alginate, line EE shows web strength of 50:50 cotton/alginate and line FF shows web strength of 50:50 nylon/alginate fabrics. In FIG. 8, line GG shows web strength of water saturated 100% alginate fabric, line HH shows web strength of water saturated 50:50 rayon/alginate, line JJ shows web strength of water saturated 50:50 cotton/alginate, line KK shows web strength of water saturated 50:50 nylon/alginate, line LL shows web strength of saline saturated 100% alginate fabric, line MM shows web strength of saline saturated 50:50 rayon/alginate, line NN shows web strength of saline saturated 50:50 cotton/alginate and line PP shows web strength of saline saturated 50:50 nylon/alginate fabric.

Figure 9:
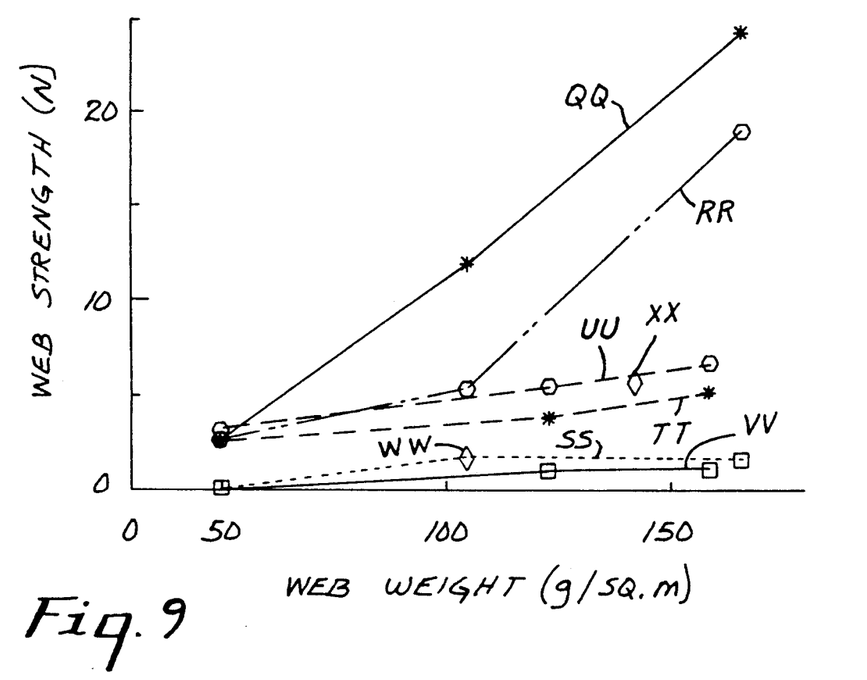
FIG. 9 plots web weight vs. web strength for fabrics made under low and high energy hydroentanglement conditions.

FIG. 9 is a comparison of the effect of hydroentanglement conditions on wet and dry strength of 100% alginate webs. The solid lines show the web strength of fabrics prepared under high energy hydroentanglement conditions, as described in Examples 46-48. Line QQ shows dry web strength, line RR shows water saturated web strength and line SS shows saline saturated web strength. The dashed lines show the web strength of fabrics prepared under low energy hydroentanglement conditions, as described in Examples 49-51. Line TT shows dry web strength, line UU shows water saturated web strength and line VV shows saline saturated web strength. The low energy hydroentanglement conditions (examples 49-51) resulted in fabrics having dry strength similar to the dry strength of competitive non-hydroentangled alginate dressing Sorbsan TM (point WW, web weight=105 g/m$^2$ and dry web strength=1.5 N), and inferior to the dry strength of competitive non-hydroentangled alginate dressing Kaltostat TM (point XX, web weight=142 g/m$^2$ and dry web strength=5.7 N). Wet strengths of low energy hydroentangled fabrics in both water and saline also were low as compared to fabrics prepared using high energy parameters.

TEST METHODS - EXAMPLES 1-24

Web Dry Strength

Web Dry Strength is determined by placing a 1.3 cm×5 cm sample (lengthwise fiber orientation) in an Instron TM tensile tester, having an initial jaw spacing of 2.54 cm, and elongating the sample at a rate of 25.4 cm/minute. The maximum load before break (average of four samples) is recorded.

Web Wet Strength

Web wet strength is determined as described above for determining the Web Dry Strength except that the web sample is immersed in a 0.9% (w/w) aqueous saline solution for 10 minutes and blotted prior to placing it in the tensile tester.

Serum Uptake

Serum Uptake is determined by immersing a pre-weighed 2.54 cm×2.54 cm web sample in bovine calf serum for 10 minutes at room temperature and then weighing the sample immediately upon removal from the serum. Reported Serum Uptake values are the average of three samples.

Nonwoven Web Preparation

Nonwoven webs are prepared by processing calcium alginate fibers (5 cm in length, 2.5-3.0 denier, 16-18% moisture content, available from Courtaulds Fibers Ltd., Coventry U.K.) in either a Rando-Webber Model #12BS or a Hergeth-Hollingsworth Card Type WZM/KS-D2-R2. The webs were hydroentangled as a single ply or as multiple plies having parallel fiber orientation.

Nonwoven calcium alginate fiber webs also are available from Courtaulds Ltd.

Web Hydroentanglement

Nonwoven webs were converted into alginate wound dressings of the present invention using a Honeycomb Hydraulic Entanglement Flat-Bed Laboratory Test Unit (from Honeycomb, Inc., Biddeford, Me.) fitted with a single head. Nonwoven web samples (prepared as described above) were placed on the wire support screen of the unit, pre-wet with water and passed at a rate of 15.25 meters/hour beneath a curtain of pressurized water. Multiple pass entanglement, up to a maximum of four passes on one face, was achieved by reversing the direction of screen travel. The wet web was removed from the support screen and dried in a circulating air oven at about 65° C. until the web was dry to the touch (approximately 30 minutes).

EXAMPLES 1-21

Alginate wound dressings of the present invention were prepared according to "Nonwoven Web Preparation" and "Web Hydroentanglement" procedures described above, specific conditions being reported in Tables I and II.

TABLE I

| | NONWOVEN WEB DESCRIPTION | | |
|---|---|---|---|
| Example | Nonwoven Web | # of Layers | Basis Weight (g/m$_2$) |
| 1 | H | 1 | 32 |
| 2 | H | 2 | 64 |
| 3 | H | 3 | 90 |
| 4 | H | 3 | 130 |
| 5 | H | 2 | 64 |
| 6 | H | 3 | 90 |
| 7 | H | 3 | 129 |
| 8 | H | 2 | 84 |
| 9 | H | 3 | 90 |
| 10 | H | 2 | 67 |
| 11 | H | 3 | 112 |
| 12 | H | 3 | 98 |
| 13 | H | 4 | 160 |
| 14 | H | 5 | 100 |
| 15 | R | 1 | 82 |
| 16 | R | 2 | 145 |
| 17 | R | 1 | 124 |
| 18 | C | 10 | 201 |
| 19 | C | 6 | 118 |
| 20 | C | 4 | 82 |
| 21 | C | 2 | 48 | a = Basis weight of hydroentangled web
H = Hergeth-Hollingsworth
R = Rando-Webber
C = Carded web obtained from Courtaulds Ltd.

TABLE II

| | | HYDROENTANGLEMENT CONDITIONS | | | | | | | |
|---|---|---|---|---|---|---|---|---|---|
| | | SIDE 1 WATER PRESSURE (kPa) | | | | | SIDE 2 WATER PRESSURE (kPa) | | |
| Ex. | Wire Mesh$^a$ | Pass 1 | Pass 2 | Pass 3 | Pass 4 | Wire Mesh$^a$ | Pass 1 | Pass 2 | Pass 3 |
| 1 | 100 × 100 | 2100 | 4100 | 6200 | — | 20 × 20 | 2100 | 4100 | 4100 |
| 2 | 100 × 100 | 3500 | 6900 | 10300 | — | 20 × 20 | 10300 | 3500 | 3500 |
| 3 | 100 × 100 | 3500 | 6900 | 10300 | — | 20 × 20 | 10300 | 3500 | 3500 |
| 4 | 100 × 100 | 3500 | 6900 | 10300 | — | 20 × 20 | 10300 | 3500 | 3500 |
| 5 | 100 × 100 | 3500 | 6900 | 10300 | — | 14 × 14 | 10300 | 3500 | 3500 |
| 6 | 100 × 100 | 3500 | 6900 | 10300 | — | 14 × 14 | 10300 | 3500 | 3500 |
| 7 | 60 × 60 | 700 | 3500 | 9600 | 9600 | — | — | — | — |
| 8 | 60 × 60 | 700 | 3500 | 9600 | 9600 | — | — | — | — |
| 9 | 14 × 14 | 10300 | 10300 | 10300 | — | — | — | — | — |
| 10 | 14 × 14 | 700 | 3500 | 9600 | 9600 | — | — | — | — |
| 11 | 14 × 14 | 700 | 3500 | 9600 | 9600 | — | — | — | — |
| 12 | 6 × 8 | 700 | 3500 | 9600 | 9600 | — | — | — | — |
| 13 | 6 × 8 | 700 | 3500 | 9600 | 9600 | — | — | — | — |
| 14 | 6 × 8 | 700 | 3500 | 9600 | 9600 | — | — | — | — |
| 15 | 6 × 8 | 700 | 3500 | 9600 | 9600 | — | — | — | — |
| 16 | 6 × 8 | 700 | 3500 | 9600 | 9600 | — | — | — | — |
| 17 | 6 × 8 | 700 | 3500 | 9600 | 9600 | — | — | — | — |
| 18 | 6 × 8 | 700 | 3500 | 9600 | 9600 | — | — | — | — |
| 19 | 6 × 8 | 700 | 3500 | 9600 | 9600 | — | — | — | — |
| 20 | 6 × 8 | 700 | 3500 | 9600 | 9600 | — | — | — | — |
| 21 | 6 × 8 | 700 | 3500 | 9600 | 9600 | — | — | — | — |

$^a$wires/inch × wires/inch
Results of Web Dry Strength, Web Wet Strength and Serum Uptake testing of these webs are reported in Table III.

EXAMPLE 22

A single ply of a rayon staple fiber web (4 cm fiber length, 1.5 denier, 30 g/m² basis weight, formed on a Hollingsworth Card) was overlaid on a single ply of a calcium alginate staple fiber web (5 cm fiber length, 2.8 denier, 80 g/m² basis weight, formed on a Rando Webber) such that the machine direction in the two webs was parallel. The two-ply web structure was hydroentangled using a Honeycomb Entanglement unit fitted with a wire support screen having 6×8 wires per inch, using four passes beneath the pressurized water curtain at 700, 3500, 9600 and 9600 kPa, respectively. The resulting alginate fabric was removed from the screen and heated at about 65° C. until dry (approximately 30 minutes). Web Dry Strength and Web Wet Strength data are reported in Table III.

Comparative Example C1

A carded calcium alginate staple fiber web having a basis weight of 179 g/m² which had been embossed using a heated roll following carding was obtained from Courtaulds Research, Coventry, U.K. to serve as Comparative Example C1.

Comparative Examples C2–C4

C2=Sorbsan TM carded web as identified above.
C3=Kaltostat TM carded and needle-tacked web as identified above.
C4=Ultraplast TM knitted styptic gauze as identified above.

Web Dry Strength, Web Wet Strength, and Serum Uptake data for the comparative webs are reported in Table III.

TABLE III
WEB EVALUATION DATA

| Example | Basis Weight (g/m²) | Dry Web Strength (Newtons) | Dry Web Strength (N/g/m²) | Wet Web Strength (Newtons) | Wet Web Strength (N/g/m²) | Serum Uptake (g/cm²) |
|---|---|---|---|---|---|---|
| 1 | 32 | 0.49 | .015 | 0.12 | .004 | 0.07 |
| 2 | 64 | 1.78 | .028 | 1.16 | .018 | 0.13 |
| 3 | 90 | 4.72 | .052 | 4.14 | 0.46 | 0.17 |
| 4 | 130 | 3.65 | .028 | 3.20 | .025 | 0.16 |
| 5 | 64 | 0.98 | .015 | 0.62 | .010 | 0.13 |
| 6 | 90 | 1.82 | .020 | 1.74 | .019 | 0.14 |
| 7 | 129 | 5.70 | .044 | 4.85 | .036 | 0.13 |
| 8 | 84 | 2.23 | .026 | 1.65 | .020 | 0.12 |
| 9 | 90 | 2.40 | .027 | 4.14 | .046 | 0.18 |
| 10 | 67 | 1.25 | .021 | 0.93 | .014 | 0.14 |
| 11 | 112 | 3.43 | .031 | 2.23 | .020 | 0.15 |
| 12 | 98 | 2.54 | .026 | 1.56 | .016 | 0.18 |
| 13 | 160 | 4.01 | .025 | 5.07 | .032 | 0.23 |
| 14 | 100 | 2.14 | .021 | 3.16 | .032 | 0.18 |
| 15 | 82 | 2.18 | .027 | 0.53 | .006 | 0.14 |
| 16 | 145 | 8.19 | .056 | 6.27 | .043 | 0.17 |
| 17 | 124 | 7.08 | .057 | 4.72 | .038 | 0.17 |
| 18 | 201 | 8.46 | .042 | 6.50 | .032 | 0.18 |
| 19 | 118 | 4.49 | 0.38 | 2.71 | .023 | 0.16 |
| 20 | 82 | 2.54 | 0.31 | 1.07 | .013 | 0.13 |
| 21 | 48 | 1.78 | 0.37 | 0.22 | .005 | 0.11 |
| 22 | 110 | 18.02 | .164 | 13.88 | .126 | — |
| C1 | 179 | 0.36 | .002 | 0.76 | .004 | 0.40 |
| C2 | 112 | 0.45 | .004 | 0.13 | .001 | 0.29 |
| C3 | 160 | 0.71 | .004 | 2.14 | .013 | 0.41 |
| C4 | 113 | 6.63 | .059 | 0.03 | .0003 | 0.11 |

In Examples 1–22, web basis weight correlated to Web Wet Strength and Wet Dry Strength in that higher basis weight webs that were otherwise identical generally produced stronger fabrics. However, both the Web Wet Strength and Web Dry Strength of alginate wound dressings of the invention were significantly better than those of comparative Examples C1–C4, even when those of the invention were significantly lower in basis weight.

EXAMPLE 23

A blend of 0.1 g chitosan staple fiber (4 cm staple length, from Protan Laboratories, Redmond, Wash.) and 0.9 g calcium alginate staple fiber (5 cm length, 2.8 denier, from Courtaulds Fibers Ltd., Coventry, U.K.) was hand carded to provide a 10 cm×10 cm pad which was hydroentangled by the same procedure used for Example 22. After drying at about 65° C., the entangled web exhibited good integrity.

EXAMPLE 24

Application of Alginate Nonwoven Wound Dressings to Full-Thickness Excisions of Pigs Two female Yorkshire pigs weighing 35–45 kg were anesthetized using Halothane TM, nitrous oxide and oxygen, and their backs were shaved and prepared for surgery. Eight full-thickness excisions approximately 2.5 cm×2.5 cm in size were made on the backs of each animal. After hemostasis was achieved, two of the wounds on each animal were packed with 4 layers of a Sorbsan TM surgical dressing (Comparative Example C2) which had been cut into 2.5 cm×2.5 cm squares. Two of the six remaining wounds on each animal were packed with four layers of the hydroentangled alginate wound dressing of Example 8, two with four layers of the dressing of Example 9, and two with four layers of the dressing of Example 13, all of which had been sterilized by ethylene oxide and cut into 2.5 cm×2.5 cm squares. Each of the alginate-packed wounds was overdressed with a Tegaderm TM transparent film dressing (available from 3M). The pigs were then placed in protective cages to prevent disruption of the dressings and returned to their runs.

Twenty-four hours following surgery, the pigs were anesthetized to allow inspection and changing of the dressings. At that time, all of the alginate dressings had become saturated with exudate, and pooled exudate was evident beneath the Tegaderm TM dressings. After peeling away the Tegaderm TM dressing, all four layers of the alginate dressings in each wound were lifted together or picked out using forceps. The fraction of the wounds from which all four layers of the alginate dressings were lifted out of the wounds in one piece, leaving little or no residue in the wound, is reported in Table IV.

Following irrigation with saline, the wounds were redressed in the same manner as before, each wound being packed with the same type of alginate dressing used previously.

On Days 3, 5 and 7 following surgery (Day 0), the wound dressings were changed using the same procedures as on Day 1, and removability is reported in Table IV.

Histological assessment of biopsies taken on Day 9 following surgery indicated that healing progress was the same for all wounds in the study, regardless of the type of alginate dressing with which they had been dressed.

TABLE IV

| Example | Day 1 | Day 3 | Day 5 | Day 7 | Totals |
|---------|-------|-------|-------|-------|--------|
| 8 | ¼ | ¼ | ¾ | 4/4 | 9/16 |
| 9 | 0/4 | ¼ | ¾ | ¾ | 7/16 |
| 13 | 4/4 | ¼ | 2/4 | ¾ | 10/16 |
| C2 | 0/4 | 0/4 | ¼ | 2/4 | 3/16 |

TEST METHODS - EXAMPLES 25-48

Web Dry Strength

Web dry strength is determined by placing a 2.5 cm×5 cm sample (lengthwise fiber orientation) in an Instron TM Tensile Tester, having an initial jaw spacing of 2.54 cm, and elongating the sample at a rate of 25.4 cm/minute. The maximum load before break (average of three samples) is recorded.

Web Wet Strength

Web wet strength is determined as described above for determining Web Dry Strength except that the web sample is immersed in either water or a 0.9% (w/w) aqueous saline solution for 24 hours and blotted prior to placing it in the tensile tester.

Absorbency

Absorbency is determined by immersing a preweighed 2.54 cm×2.54 cm web sample in either water or 0.9% (w/w) aqueous saline solution at room temperature for 24 hours and then weighing the sample immediately upon removal from the liquid. The moisture content (average of three samples) is recorded.

Moisture Retention

Moisture retention is determined by preparing a fabric sample and immersing it in a 0.9% (w/w) aqueous saline solution as described above for determining absorbency except that after the sample has been removed from the saline bath, it is stored on a flat open tray at 25 degrees C. and 70% relative humidity. The sample is then weighed periodically. The moisture content (average of three samples) after each time period is recorded.

Web Preparation and Entanglement

Staple fibers were combined in the hopper of a Rando-Webber Model #12BS, according to the type and ratio (by weight) listed in Table V. When the fiber appeared to be sufficiently opened and blended, it was fed through the Rando-Webber to form a nonwoven web. The nonwoven webs were then hydroentangled as a single ply or multiple plies having parallel fiber orientation using a Honeycomb Hydraulic Entanglement Flat-Bed Laboratory Unit (from Honeycomb, Inc. Biddeford, Me.). Each sample was subjected to one hydroentanglement pass at 700 kPa, one pass at 3500 kPa and 2 passes at 9600 kPa, all on the same side of the web, at a web speed of about 10 meters per minute, using a 12×14 mesh polyester screen. Excess water was removed from the webs using the vacuum slot of the Honeycomb hydroentangler. The webs were then placed in a circulating air oven at 50 degrees C. for about 12 hours.

Materials used were calcium alginate staple fiber, 2.5-3.0 denier×5 cm., 15-20% moisture content from Courtaulds Fibers Ltd., Coventry, U.K.; rayon staple fiber, 1.5 denier×5 cm., from Courtaulds Fibers Ltd., Coventry, U.K.; cotton fiber, type V102B; and nylon fiber, type T-201, 3.0 denier×5 cm., from DuPont.

Comparative Examples 49-51

(Low Energy Hydroentanglement)

Examples 49-51 were prepared as described above for examples 25-48, but with modification of the hydroentanglement conditions. Examples 49-51 were subjected to two hydroentanglement passes at 1400 kPa and four passes at 2750 kPa, all on the same side of the web and at a web speed of 41 meters per minute.

EXAMPLE 52

A single ply of a rayon staple fiber web (58 g/sq. m web weight) formed on a Rando-Webber) was overlaid with a single ply of a calcium alginate staple fiber web (26 g/sq. m web weight, formed on a Hollingsworth Card) such that the machine direction in the two webs is parallel. The two ply web-structure was hydroentangled and dried as described above for Examples 25-48.

EXAMPLE 53

A single ply of a cotton fiber web (55 g/sq. m web weight, formed on a Rando-Webber) was overlaid with a single ply of a calcium alginate staple fiber web (26 g/sq. m, formed on a Hollingsworth card) such that the machine direction in the two webs is parallel. The two ply web-structure was hydroentangled and dried as described above for Examples 25-48.

TABLE V

| EXAMPLE | FIBER RATIO & TYPE | WEB WEIGHT g/sq m | DRY STRENGTH N | WET STRENGTH (24-h saline) N | WET STRENGTH (24-h water) N | ABSORBENCY (24-h saline) % | ABSORBENCY (24-h water) % |
|---------|--------------------|-----|-------|-------|-------|---------|---------|
| 25 | 100% Alginate | 108.00 | 15.12 | 1.82 | 13.79 | 2165.00 | 760.00 |
| 26 | 20:80 Rayon Alginate | 119.00 | 30.69 | 10.68 | 22.24 | 1635.00 | 851.00 |
| 27 | 30:60 Rayon Alginate | 128.00 | 47.15 | 17.79 | 36.03 | 1753.00 | 837.00 |
| 28 | 50:50 Rayon Alginate | 138.00 | 44.93 | 19.57 | 38.26 | 1580.00 | 898.00 |
| 29 | 60:30 Rayon Alginate | 129.00 | 61.83 | 32.92 | 43.59 | 1469.00 | 962.00 |
| 30 | 80:20 Rayon Alginate | 108.00 | 43.15 | 28.91 | 37.81 | 1424.00 | 1089.00 |
| 31 | 100% Rayon | 112.00 | 53.83 | 38.26 | 41.37 | 1125.00 | 1021.00 |
| 32 | 20:80 Cotton Alginate | 48.00 | 6.23 | 2.00 | 5.65 | 2730.00 | 916.00 |
| 33 | 20:80 Cotton Alginate | 110.00 | 17.79 | 7.25 | 20.91 | 1518.00 | 767.00 |
| 34 | 20:80 Cotton | 157.00 | 32.47 | 4.54 | 35.14 | 1147.00 | 685.00 |

TABLE V-continued

| EXAMPLE | FIBER RATIO & TYPE | WEB WEIGHT g/sq m | DRY STRENGTH N | WET STRENGTH (24-h saline) N | WET STRENGTH (24-h water) N | ABSORBENCY (24-h saline) % | ABSORBENCY (24-h water) % |
|---|---|---|---|---|---|---|---|
| 35 | 50:50 Cotton Alginate | 44.00 | 6.67 | 2.58 | 8.90 | 2077.00 | 1466.00 |
| 36 | 50:50 Cotton Alginate | 88.00 | 19.57 | 9.34 | 24.91 | 1487.00 | 1037.00 |
| 37 | 50:50 Cotton Alginate | 119.00 | 26.25 | 14.46 | 29.80 | 1412.00 | 899.00 |
| 38 | 50:50 Cotton Alginate | 138.00 | 37.37 | 21.35 | 46.71 | 1227.00 | 812.00 |
| 39 | 50:50 Cotton Alginate | 195.00 | 46.71 | 22.69 | 58.27 | 1488.00 | 891.00 |
| 40 | 50:50 Rayon Alginate | 44.00 | 11.57 | 10.23 | 18.24 | 2546.00 | 1332.00 |
| 41 | 50:50 Rayon Alginate | 98.00 | 43.59 | 19.13 | 29.80 | 1441.00 | 985.00 |
| 42 | 50:50 Rayon Alginate | 192.00 | 90.75 | 47.60 | 61.39 | 1059.00 | 828.00 |
| 43 | 50:50 Nylon Alginate | 66.00 | 15.57 | 1.47 | 14.68 | 2047.00 | 1404.00 |
| 44 | 50:50 Nylon Alginate | 135.00 | 48.49 | 6.49 | 47.60 | 1451.00 | 964.00 |
| 45 | 50:50 Nylon Alginate | 209.00 | 79.18 | 4.14 | 76.96 | 1290.00 | 811.00 |
| 46 | 100% Alginate | 50.00 | 2.67 | 0.00 | 2.67 | disintegrated | 1294.00 |
| 47 | 100% Alginate | 105.00 | 12.01 | 1.91 | 5.43 | 1730.00 | 894.00 |
| 48 | 100% Alginate | 166.00 | 24.47 | 1.60 | 19.13 | 1350.00 | 683.00 |
| 49 | 100% Alginate | 50.00 | 2.54 | 0.00 | 3.20 | disintegrated | 1186.00 |
| 50 | 100% Alginate | 123.00 | 4.00 | 1.02 | 5.47 | disintegrated | 1120.00 |
| 51 | 100% Alginate | 159.00 | 5.34 | 1.16 | 6.67 | 1996.00 | 1204.00 |

TABLE VI

| EXAMPLE | FIBER RATIO & TYPE | WEB WEIGHT g/sq m | MOISTURE RETENTION | | | | | | |
|---|---|---|---|---|---|---|---|---|---|
| | | | T = 0 h % | T = 1 h % | T = 2 h % | T = 4 h % | T = 6 h % | T = 8 h % | T = 24 h % |
| 25 | 100% Alginate | 108.00 | 2165.00 | 1123.00 | 916.00 | 470.00 | 161.00 | 37.00 | 7.00 |
| 26 | 20:80 Rayon Alginate | 119.00 | 1635.00 | 1206.00 | 910.00 | 488.00 | 176.00 | 19.00 | 6.00 |
| 27 | 30:60 Rayon Alginate | 128.00 | 1753.00 | 1218.00 | 1007.00 | 571.00 | 254.00 | 51.00 | 10.00 |
| 28 | 50:50 Rayon Alginate | 138.00 | 1580.00 | 1150.00 | 964.00 | 531.00 | 219.00 | 35.00 | 10.00 |
| 29 | 60:30 Rayon Alginate | 129.00 | 1469.00 | 967.00 | 765.00 | 310.00 | 30.00 | 10.00 | 11.00 |
| 30 | 80:20 Rayon Alginate | 108.00 | 1424.00 | 698.00 | 462.00 | 15.00 | 12.00 | 11.00 | 13.00 |
| 31 | 100% Rayon | 112.00 | 1125.00 | 685.00 | 482.00 | 36.00 | 18.00 | 18.00 | 19.00 |
| 32 | 20:80 Cotton Alginate | 48.00 | 2075.00 | 1369.00 | 999.00 | 271.00 | 19.00 | 17.00 | 16.00 |
| 33 | 20:80 Cotton Alginate | 110.00 | 1183.00 | 1140.00 | 717.00 | 383.00 | 36.00 | 12.00 | 9.00 |
| 34 | 20:80 Cotton Alginate | 157.00 | 995.00 | 775.00 | 668.00 | 414.00 | 85.00 | 14.00 | 11.00 |
| 35 | 50:50 Cotton Alginate | 44.00 | 1824.00 | 1050.00 | 665.00 | 21.00 | 15.00 | 15.00 | 14.00 |
| 36 | 50:50 Cotton Alginate | 88.00 | 1311.00 | 933.00 | 754.00 | 326.00 | 11.00 | 10.00 | 9.00 |
| 37 | 50:50 Cotton Alginate | 119.00 | 1176.00 | 865.00 | 713.00 | 374.00 | 29.00 | 16.00 | 15.00 |
| 38 | 50:50 Cotton Alginate | 138.00 | 1091.00 | 918.00 | 795.00 | 516.00 | 165.00 | 18.00 | 13.00 |
| 39 | 50:50 Cotton Alginate | 195.00 | 1053.00 | 883.00 | 792.00 | 582.00 | 314.00 | 134.00 | 25.00 |
| 40 | 50:50 Rayon Alginate | 44.00 | 1943.00 | 1331.00 | 893.00 | 84.00 | 29.00 | 27.00 | 26.00 |
| 41 | 50:50 Rayon Alginate | 98.00 | 1304.00 | 936.00 | 696.00 | 184.00 | 16.00 | 16.00 | 15.00 |
| 42 | 50:50 Rayon Alginate | 192.00 | 967.00 | 767.00 | 641.00 | 371.00 | 79.00 | 14.00 | 12.00 |
| 43 | 50:50 Nylon Alginate | 66.00 | 1681.00 | 1130.00 | 804.00 | 138.00 | 40.00 | 39.00 | 37.00 |
| 44 | 50:50 Nylon Alginate | 135.00 | 1183.00 | 950.00 | 761.00 | 339.00 | 25.00 | 16.00 | 14.00 |
| 45 | 50:50 Nylon Alginate | 209.00 | 977.00 | 798.00 | 656.00 | 357.00 | 94.00 | 36.00 | 32.00 |
| 46 | 100% Alginate | 50.00 | 2433.00 | 2012.00 | 1607.00 | 819.00 | 297.00 | 180.00 | 57.00 |

TABLE VI-continued

| EXAMPLE | FIBER RATIO & TYPE | WEB WEIGHT g/sq m | MOISTURE RETENTION | | | | | | |
|---|---|---|---|---|---|---|---|---|---|
| | | | T = 0 h % | T = 1 h % | T = 2 h % | T = 4 h % | T = 6 h % | T = 8 h % | T = 24 h % |
| 47 | 100% Alginate | 105.00 | 1378.00 | 1131.00 | 856.00 | 375.00 | 51.00 | 38.00 | 32.00 |
| 48 | 100% Alginate | 166.00 | 983.00 | 764.00 | 583.00 | 210.00 | 37.00 | 34.00 | 31.00 |
| 49 | 100% Alginate | 50.00 | | | | Disintegrated | | | |
| 50 | 100% Alginate | 123.00 | | | | Disintegrated | | | |
| 51 | 100% Alginate | 159.00 | 1759.00 | 1531.00 | 1337.00 | 934.00 | 551.00 | 341.00 | 4.00 |

Alginate fabrics of the invention can be made by methods other than as described above. For example, they can be made by creating a nonwoven web of alginate fibers by the method of the above-cited Tong patent and then hydroentangling the fibers of that web.

We claim:

1. A wound dressing comprising a nonwoven fabric consisting of at least 35% by weight of alginate staple fibers, which fabric is substantially free from any adhesive binder or of interfusing of fibers at their crossing points, said fibers being sufficiently entangled that a plot of the fabric's tensile strength vs. basis weight lies above line 12 of FIG. 1 of the drawing when the fabric is dry and lies above line 22 of FIG. 2 when the fabric is saturated with saline water.

2. A wound dressing as defined in claim 1 wherein the nonwoven fabric has a basis weight of at least 20 g/m$^2$.

3. A wound dressing as defined in claim 2, the fabric of which has a basis weight of from 50 to 180 g/m$^2$.

4. A wound dressing as defined in claim 3, the fabric of which has a basis weight of at least 60 g/m$^2$ and has sufficient integrity to permit it to be converted into strips as narrow as 5 mm using a continuous slitting process.

5. A wound dressing as defined in claim 1, wherein substantially all of the staple alginate fibers of the nonwoven fabric are from 2 to 10 cm in length.

6. A wound dressing as defined in claim 1 wherein the fabric further comprises reinforcing fibers.

7. A wound dressing as defined in claim 1 wherein the fabric further comprises chitosan fibers.

8. A wound dressing as defined in claim 1 and having a highly open structure so that when the dressing is saturated with saline fluids, it is sufficiently translucent in contact with a wound to permit the wound to be inspected without removing the dressing.

9. A wound dressing as defined in claim 1 and containing at least one therapeutic agent.

10. A wound dressing comprising a nonwoven fabric comprising at least 35% by weight of alginate staple fibers, which fabric is substantially free from any adhesive binder or of interfusing of fibers at their crossing points, said fibers being sufficiently entangled that the fabric has a Web Dry Strength of at least 0.01 N/g/m$^2$ and a Web Wet Strength of at least as herein defined of at least 0.005 N/g/m$^2$.

11. A wound dressing as defined in claim 10 wherein the Web Dry Strength is at least 0.03 N/g/m$^2$.

12. A wound dressing as defined in claim 10 wherein the Web Wet Strength is at least 0.02 N/g/m$^2$.

13. A method of dressing a wound comprising the steps of:
(a) preparing an alginate wound dressing comprising a nonwoven fabric comprising at least 35% by weight of alginate staple fibers, which fabric is substantially free from any adhesive binder or of interfusing of fibers at their crossing points, said fibers being sufficiently entangled that a plot of the fabric's tensile strength vs. basis weight lies above line 12 of FIG. 1 of the drawing when the fabric is dry and lies above line 22 of FIG. 2 of the drawing when the fabric is saturated with saline water, and
(b) applying that wound dressing to the wound.

14. A method as defined in claim 13 and including prior to step (b) the step of saturating the alginate wound dressing with saline fluid.

15. A method as defined in claim 13 and including the step of covering the wound dressing applied in step (b) with a material selected from film dressings, gauze dressings, hydrocolloid dressings, and bandage wraps.

16. A wound dressing as defined in claim 1 wherein the nonwoven fabric retains measurable saline moisture for at least 6 hours after it is removed from the saline bath, stored on a flat open tray at 25 degrees C. and 70% relative humidity.

17. A wound dressing as defined in claim 1 wherein the nonwoven fabric comprises at least 50% by weight of alginate fibers.

18. A wound dressing as defined in claim 1 wherein the balance of the fabric comprises a fiber selected from the group consisting of rayon, cotton or nylon.

19. A wound dressing comprising a nonwoven fabric of layered fiber webs, wherein at least one layer is a predominantly alginate fiber web and one layer is a fiber web that is not predominantly alginate fiber, which fabric is substantially free from any adhesive binder or of interfusing of fibers at their crossing points, said fibers being sufficiently entangled that a plot of the fabric's tensile strength vs. basis weight lies above line 12 of FIG. 1 of the drawing when the fabric is dry and lies above line 22 of FIG. 2 when the fabric is saturated with saline water.

20. A wound dressing as defined in claim 19 wherein the layer of predominantly alginate fiber web is more than about 10% by weight of the total fabric.

21. A wound dressing as defined in claim 19 wherein the layer of fiber web that is not predominantly alginate fiber is located between two layers of predominantly alginate fiber web.

* * * * *